(12) United States Patent
Sugiue et al.

(10) Patent No.: US 9,817,009 B2
(45) Date of Patent: Nov. 14, 2017

(54) BIOLOGICAL INFORMATION MEASUREMENT DEVICE

(71) Applicant: Panasonic Healthcare Holdings Co., Ltd., Minato-ku, Tokyo (JP)

(72) Inventors: Yuichi Sugiue, Ehime (JP); Hiroshi Andoh, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 347 days.

(21) Appl. No.: 14/430,546

(22) PCT Filed: Sep. 27, 2013

(86) PCT No.: PCT/JP2013/005781
§ 371 (c)(1),
(2) Date: Mar. 23, 2015

(87) PCT Pub. No.: WO2014/057625
PCT Pub. Date: Apr. 17, 2014

(65) Prior Publication Data
US 2015/0253346 A1    Sep. 10, 2015

(30) Foreign Application Priority Data
Oct. 10, 2012 (JP) .................................. 2012-224771

(51) Int. Cl.
*G01N 33/49* (2006.01)
*G01N 15/06* (2006.01)
(Continued)

(52) U.S. Cl.
CPC ..... *G01N 35/0092* (2013.01); *A61B 5/14532* (2013.01); *G01N 33/49* (2013.01);
(Continued)

(58) Field of Classification Search
CPC .... G01N 35/0092; G01N 33/49; G01N 15/06; G01N 33/00; G01N 33/48; A61B 5/14532
(Continued)

(56) References Cited

U.S. PATENT DOCUMENTS

| 5,243,516 A | 9/1993 | White et al. |
| 7,351,323 B2 | 4/2008 | Iketaki et al. |

(Continued)

FOREIGN PATENT DOCUMENTS

| JP | H5-502727 A | 5/1993 |
| JP | 2012-53061 A | 3/2012 |

(Continued)

OTHER PUBLICATIONS

PCT International Search Report of Int'l Appln. No. PCT/JP2013/005781 dated Dec. 10, 2013.

*Primary Examiner* — Brian J Sines
(74) *Attorney, Agent, or Firm* — Shinjyu Global IP

(57) ABSTRACT

It is an object of certain embodiments of the present invention to suppress variance in measurement results from a biological information measurement device and enhance measurement accuracy. A biological information measurement device comprises a main case having a sensor mounting component for mounting a sensor that senses biological information, a measurement component that connects to the sensor mounting component, a controller that connects to the measurement component, a first timer that connects to the controller, and a second timer that connects to the controller. The controller has a measurement mode in which a measurement operation is performed through the measurement component. In the measurement mode, the controller executes the measurement operation based on a preset measurement timing using the first timer, and determines the suitability of the measurement operation based on the preset measurement timing, using the second timer.

14 Claims, 3 Drawing Sheets

(51) Int. Cl.
  *G01N 33/00* (2006.01)
  *G01N 33/48* (2006.01)
  *G01N 35/00* (2006.01)
  *G01N 33/543* (2006.01)
  *G01N 33/66* (2006.01)
  *A61B 5/145* (2006.01)

(52) U.S. Cl.
  CPC ......... *G01N 33/5438* (2013.01); *G01N 33/66* (2013.01); *G01N 35/00584* (2013.01); *G01N 2035/00891* (2013.01)

(58) Field of Classification Search
  USPC ................ 422/68.1, 82.01, 82.05, 502, 509; 436/43, 63, 66, 50, 95, 149, 164; 600/300, 365
  See application file for complete search history.

(56) References Cited

U.S. PATENT DOCUMENTS

| | | | |
|---|---|---|---|
| 8,344,733 B2 | 1/2013 | Nakamura et al. | |
| 2005/0023137 A1* | 2/2005 | Bhullar | G01N 27/3272 204/403.1 |
| 2005/0109637 A1* | 5/2005 | Iyengar | A61B 5/14532 205/775 |
| 2005/0258034 A1 | 11/2005 | Iketaki et al. | |
| 2006/0224658 A1* | 10/2006 | Sato | G01N 27/3274 708/801 |
| 2006/0231421 A1* | 10/2006 | Diamond | C12Q 1/006 205/777.5 |
| 2006/0231424 A1* | 10/2006 | Harding | G01N 27/3273 205/792 |
| 2006/0231425 A1* | 10/2006 | Harding | C12Q 1/006 205/792 |
| 2009/0205976 A1* | 8/2009 | Yoshioka | G01N 27/3274 205/775 |
| 2010/0283488 A1 | 11/2010 | Nakamura et al. | |
| 2013/0105334 A1 | 5/2013 | Nakamura et al. | |
| 2013/0204108 A1* | 8/2013 | Yoshioka | G01N 27/3274 600/347 |
| 2013/0220836 A1* | 8/2013 | Kermani | A61B 5/14532 205/782 |
| 2013/0306474 A1* | 11/2013 | Yoshioka | G01N 27/3271 204/403.01 |

FOREIGN PATENT DOCUMENTS

| | | |
|---|---|---|
| WO | 2002-57768 A1 | 7/2002 |
| WO | 2011-151953 A1 | 12/2011 |

\* cited by examiner

BIOLOGICAL INFORMATION MEASUREMENT DEVICE

PRIORITY

This is a National Stage Application under 35 U.S.C. §365 of International Application PCT/JP2013/005781, with an international filing date of Sep. 27, 2013, which claims priority to Japanese Patent Application No. 2012-224771 filed on Oct. 10, 2012. The entire disclosures of International Application PCT/JP2013/005781 and Japanese Patent Application No. 2012-224771 are hereby incorporated herein by reference.

TECHNICAL FIELD

The present disclosure relates to a biological information measurement device for measuring biological information such as the glucose level in blood, for example.

BACKGROUND ART

There are conventional biological information measurement devices that comprise, for example, a main case having a mounting component for a biological information measurement sensor, a measurement component that connects to the mounting component, a controller that connects to the measurement component, and a timer that connects to the controller. With a biological information measurement device such as this, the controller executes a measurement mode in which the measurement component measures biological information. In this measurement mode, the biological information measurement device executes a measurement operation based on a measurement timing set in advance by using the timer, and computes a blood glucose level from this measurement value (see Patent Literature 1, for example).

CITATION LIST

Patent Literature

Patent Literature 1: Published Japanese Translation of PCT International Publication for Patent Application No. Heisei 5-502727

SUMMARY

Technical Problem

With a conventional biological information measurement device, the measurement of biological information is executed using a timer, and a blood glucose level is calculated on the basis of the measurement value.

With this type of biological information measurement device, however, there may be situations, albeit extremely rare, in which the measurement is not executed at the preset timing. The cause of this is difficult to identify, partially because it happens so rarely. However, some of the causes that are currently being considered as a possibility include the measurement environment and the power supply voltage. Although the cause has yet to be identified, there is a need for some way of dealing with the problem. That is, if the measurement is not executed at the preset timing, there will be variance in the blood glucose level that is ultimately calculated, and it may be impossible to execute the measurement accurately, and this needs to be prevented.

The biological information measurement device disclosed herein provides a biological information measurement device that is effective at increasing measurement accuracy.

Solution to Problem

The biological information measurement device pertaining to a first aspect of this disclosure comprises a main case including a sensor mounting component configured to mount a sensor that senses biological information, a measurement component that connects to the sensor mounting component, a controller that connects to the measurement component, a first timer that connects to the controller, and a second timer that connects to the controller. The controller has a measurement mode in which a measurement operation is performed through the measurement component. In the measurement mode, the controller executes the measurement operation based on a preset measurement timing using the first timer, and determines the suitability of the measurement operation based on the preset measurement timing, using the second timer.

The biological information measurement device pertaining to a second aspect of this disclosure comprises a main case, a sensor mounting component, a measurement component, a controller, a first timer, and a second timer. The sensor mounting component is provided at the main case and is configured to mount a sensor that senses biological information. The measurement component connects to the sensor mounting component and measures the biological information. The controller connects to the measurement component and causes the measurement component to measure the biological information. The first timer connects to the controller and acquires at least one preset first measurement timing at which the measurement component measures the biological information. The second timer connects to the controller and acquires a second measurement timing at which the measurement component measures the biological information on the basis of the first measurement timing. The controller determines a discrepancy between the first measurement timing and the second measurement timing, and completes the measurement of the biological information by the measurement component only when the discrepancy is within a specific range.

Advantageous Effects

The biological information measurement device disclosed herein is effective at increasing measurement accuracy.

DETAILED DESCRIPTION

Embodiments will now be described in detail through reference to the drawings as needed. However, some unnecessary detailed description may be omitted. For example, detailed description of already known facts or redundant description of components that are substantially the same may be omitted. This is to avoid unnecessary repetition in the following description, and facilitate an understanding on the part of a person skilled in the art. The inventors have provided the appended drawings and the following description so that a person skilled in the art might fully understand this disclosure, but do not intend for these to limit what is discussed in the patent claims.

Figure 1:
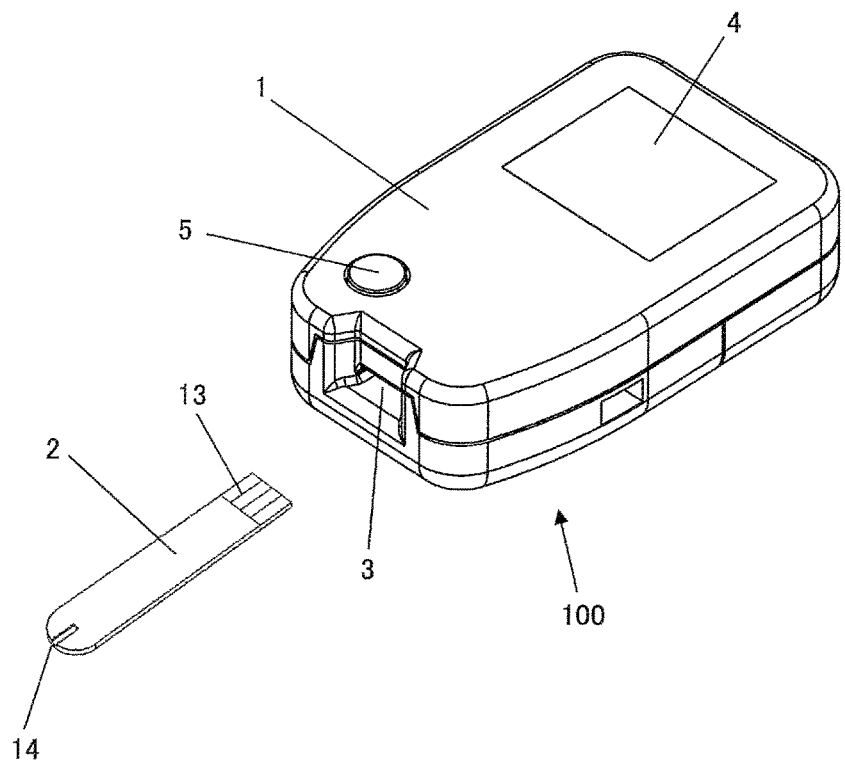
FIG. 1 is an oblique view of the biological information measurement device pertaining to Embodiment 1.

FIG. 1 is a simplified view of the exterior of a measurement device 100 (an example of a biological information measurement device) pertaining to Embodiment 1. The measurement device 100 measures the glucose level in blood (an example of biological information). The measurement device 100 comprises a main case 1 (an example of a main case).

The main case 1 is formed in a substantially rectangular shape, and has at one end a sensor mounting component 3 for mounting a blood glucose level sensor 2 (an example of a sensor) in the form of a slender plate. A power switch 5 is provided at one end on the outer surface of the main case 1, and a display component 4 (an example of a display component) is provided at the other end.

Figure 2:
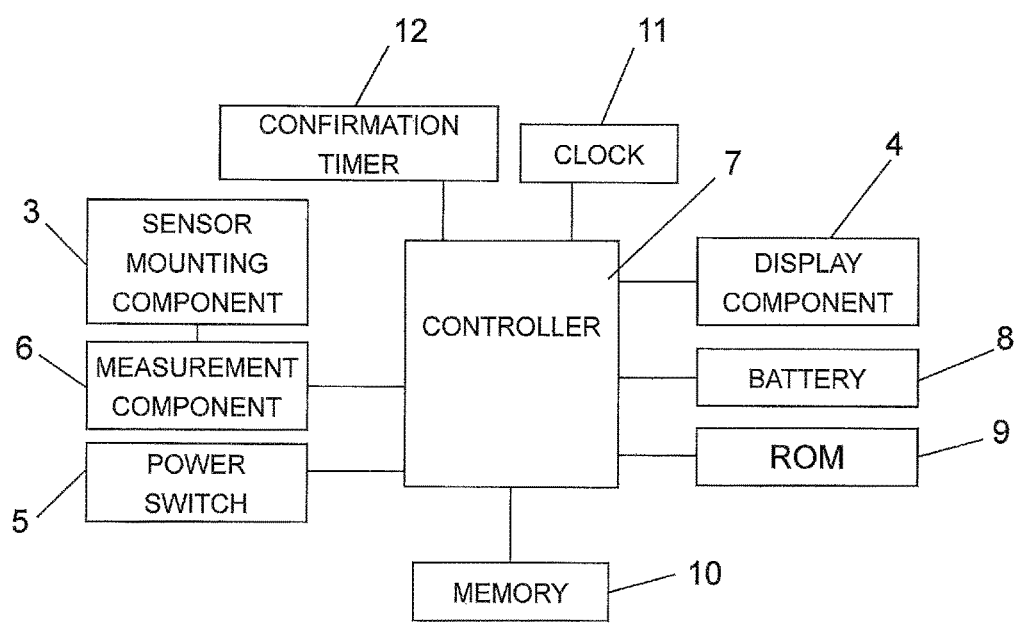
FIG. 2 is a block diagram of the biological information measurement device.

FIG. 2 is a simplified diagram of the internal configuration of the measurement device 100. As shown in FIG. 2, the main case 1 includes a measurement component 6 (an example of a measurement component) that is electrically connected to the sensor mounting component 3, and a controller 7 (an example of a controller) that connects to the measurement component 6. The controller 7 connects to the display component 4, the power switch 5, a battery 8, a ROM 9 that stores a control program for the controller 7, and a memory 10.

The controller 7 also connects to a clock 11 (an example of a first timer). The clock 11 is constituted by a quartz oscillator, for example, and therefore provides precise time and duration. The controller 7 uses the time and duration from this clock 11 to execute various control operations.

The controller 7 also executes a measurement mode in which a measurement operation is performed through the measurement component 6. In this measurement mode, a measurement operation is executed on the basis of a plurality of measurement timings that have been set in advance by using the timer function of the clock 11 (an example of a first timer). The timer, with respect to this example, uses a function where it counts upwards. A typical clock 11 using a downwards counting function may also be used.

The measurement component 6 calculates a blood glucose level from a plurality of measurement values obtained on the basis of a plurality of measurement timings, and this blood glucose level is displayed on the display component 4.

Although it rarely happens, during this measurement there may be a situation in which measurement is not executed at the preset timing. The cause of this is difficult to identify, partially because it happens so rarely. However, some of the causes that are currently being considered as a possibility include the measurement environment and the power supply voltage. Although the cause has yet to be identified, there is a need for some way of dealing with the problem. That is, if the measurement is not executed at the preset timing, there may be variance in the blood glucose level that is ultimately calculated, and this needs to be suppressed.

In view of this, the controller 7 in this embodiment connects to a confirmation timer 12 (an example of a second timer) that confirms the suitability of measurement based on a plurality of preset measurement timings. The controller 7 uses the confirmation timer 12 to determine whether or not there is a discrepancy between the actual measurement timing and the preset measurement timing for the measurement component 6 in the measurement mode. The confirmation timer 12 here is a count-up timer constituted by a ceramic oscillator, for example.

As will be discussed in detail below, because of the above configuration, the measurement device 100 can confirm from the confirmation timer 12 whether or not the measurement executed using the clock 11 has been executed properly at the measurement timing set by the controller 7, that is, whether or not there is a discrepancy between the preset measurement timing (an example of a first measurement timing) and the actual measurement timing (an example of a second measurement timing). This means that variance in the measurement result can be suppressed.

For example, when measurement by the measurement component 6 is not executed on the basis of the measurement timing preset by the controller 7, the user can be prompted by the display component 4 to take another measurement. In this way, the proper measurement can thereby be executed, and this improves the accuracy of the measurement result.

As mentioned above, the confirmation timer 12 is a count-up timer consisting of a ceramic oscillator, and makes 1000 counts per second, for example. A ceramic oscillator is not as accurate as the quartz oscillator of the clock 11, but the difference is only noticeable in units of months or years, and the accuracy is more than adequate for the few seconds that the measurement takes.

The operation of the measurement device 100 configured as above will now be described through reference to FIG. 3.

When a blood glucose level is measured, first the user presses the power switch 5 shown in FIG. 1 to turn on the power, and mounts a terminal 13 provided at one end of the blood glucose level sensor 2 to the sensor mounting component 3. This mechanically and electrically connects the terminal 13 to the sensor mounting component 3, and completes measurement preparation (S1 in FIG. 3).

The measurement component 6 applies voltage to the terminal 13 of the blood glucose level sensor 2, detects the current flowing through the blood glucose level sensor 2, converts the current into voltage (current-voltage conversion), and measures the voltage value.

Then, when the user deposits blood on a deposition part 14 provided at the other end of the blood glucose level sensor 2, the blood reacts with the reagent (not shown) on the blood glucose level sensor 2. The measurement component 6 detects this reaction by voltage that has undergone current-voltage conversion, and as a result, the controller 7 detects that blood has been deposited on the deposition part 14 (S2 in FIG. 3).

Figure 4:
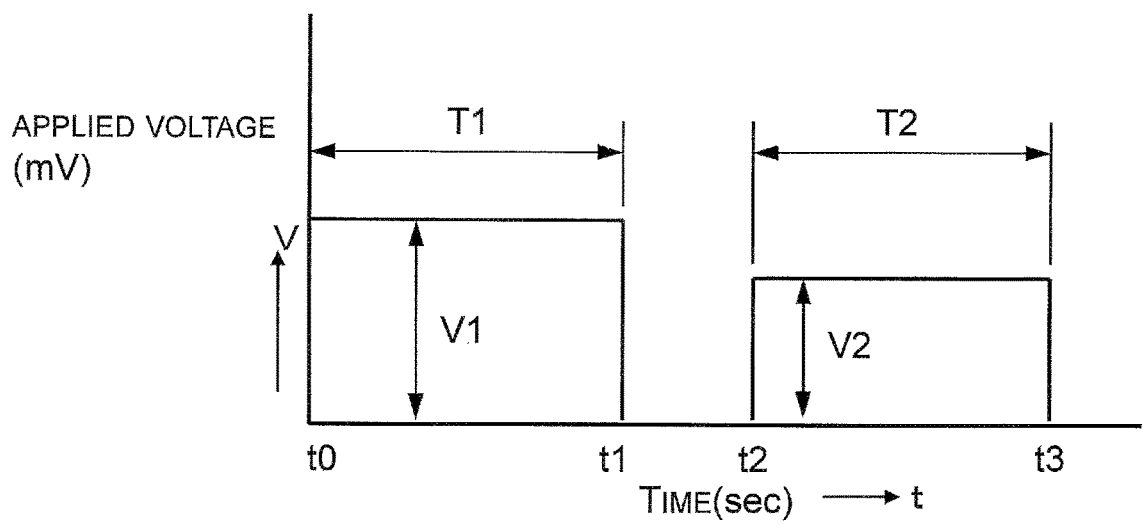
FIG. 4 is a graph of the waveform of applied voltage when measuring with the biological information measurement device.
Figure 5:
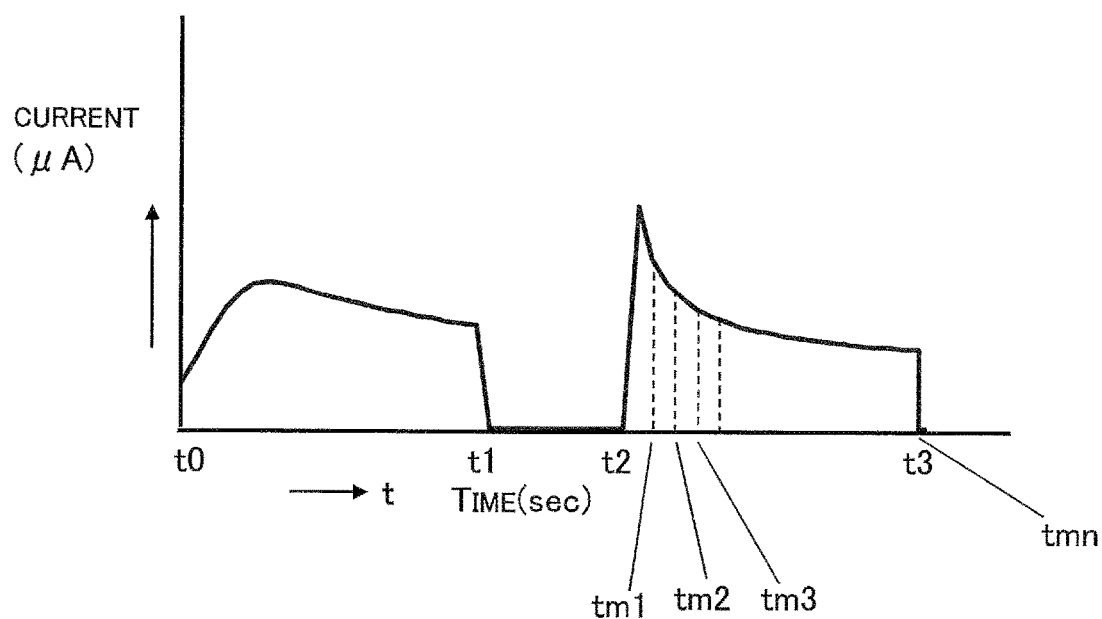
FIG. 5 is a graph of the waveform of the measurement signal when measuring with the biological information measurement device.

When the deposition of blood is detected, the controller 7 shifts into measurement mode. In the measurement mode, the controller 7 executes a blood glucose level measurement operation on the basis of a measurement timing that was set in advance by using the timer function of the clock 11. More specifically, the controller 7 uses the timer function of the clock 11 to produce voltage switch timings t0 to t3 as shown in FIG. 4, and measurement timings tm1 to tmn as shown in FIG. 5. These voltage switch timings t0 to t3 and measurement timings tm1 to tmn are stored ahead of time in the memory 10.

The voltage switch timing t0 shown in FIG. 4 is the point when measurement is started. The controller 7 actuates the confirmation timer 12 at this voltage switch timing t0. The confirmation timer 12 starts counting up at 1000 counts per second, for example. The confirmation timer 12 in this embodiment is actuated by the controller 7 immediately after the controller 7 goes into the measurement mode and the measurement of the blood glucose level is started. The confirmation timer 12 may be actuated by the controller 7 before the measurement component 6 performs actual measurement to calculate the blood glucose level (S3 in FIG. 3).

Figure 3:
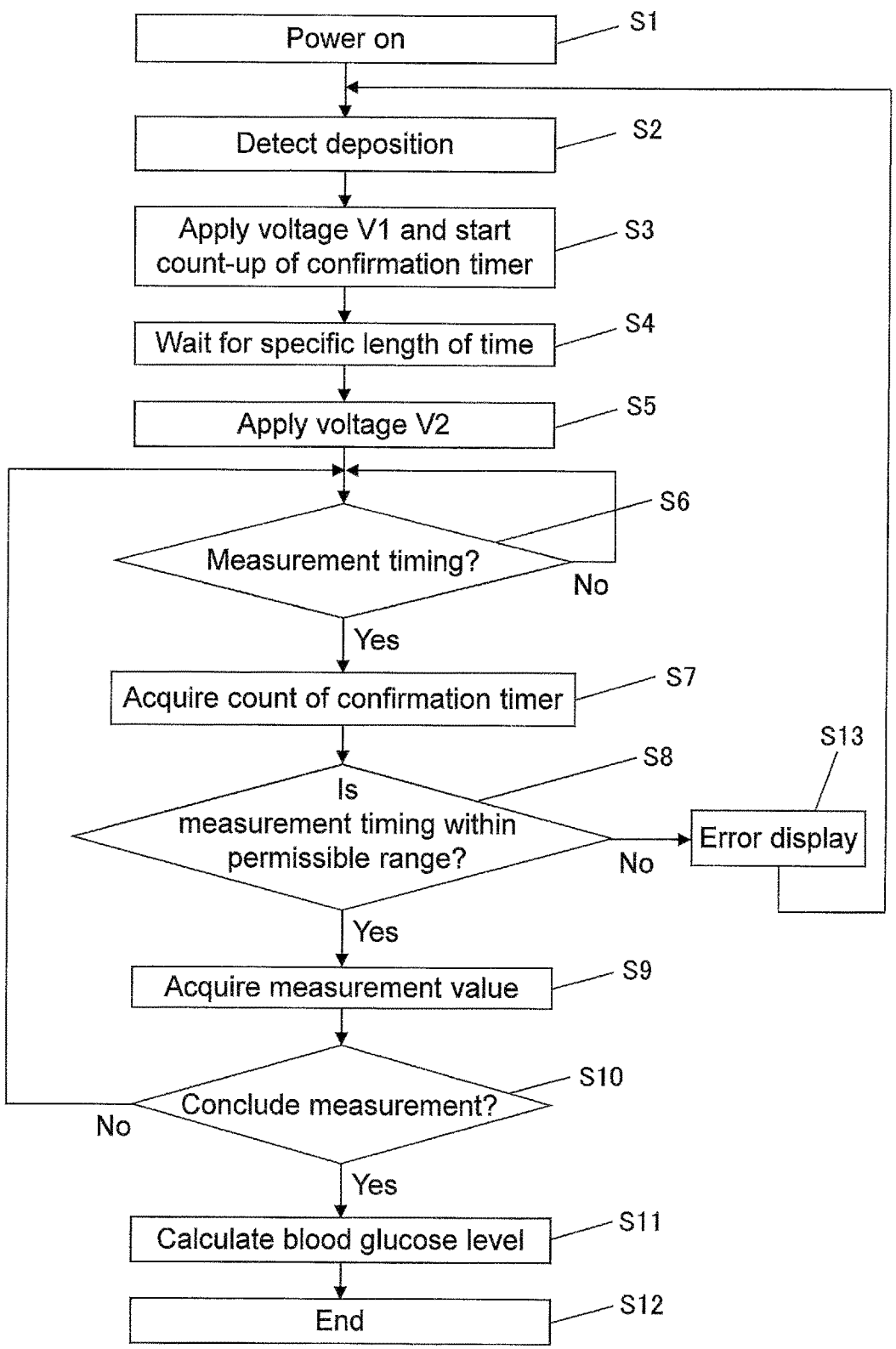
FIG. 3 is a flowchart of the operation of the biological information measurement device.

Also, the controller 7 uses the measurement component 6 to apply a voltage V1 to the terminal 13 of the blood glucose level sensor 2 for a time T1 (such as two seconds) from the voltage switch timing t0 until the voltage switch timing t1 in FIG. 4 in order to promote the reaction between the deposited blood and the reagent (not shown) on the blood glucose level sensor 2 (S3 in FIG. 3).

After this, the controller 7 ends the application of the voltage V1 at the voltage switch timing t1, and continues the reaction between the blood and the reagent (not shown) for a specific time (such as one second) from the voltage switch timing t1 until the voltage switch timing t2 (S4 in FIG. 3).

After this specific length of time (here, one second) has elapsed, the controller 7 uses the measurement component 6 to apply a measurement voltage V2 to the terminal 13 of the blood glucose level sensor 2 for a measurement time T2 (such as two seconds) from the voltage switch timing t2 until the voltage switch timing t3 (S5 in FIG. 3).

During this measurement time T2, the measurement component 6 performs a plurality of actual measurements to calculate blood glucose level.

Meanwhile, the count of the confirmation timer 12 is, for example, zero at the voltage switch timing t0, 2000 at the voltage switch timing t1, 3000 at the voltage switch timing t2, and 5000 at the voltage switch timing t3, according to the preset measurement timing. FIG. 5 shows the current waveform when the above-mentioned voltage V1 and measurement voltage V2 are applied.

The controller 7 uses the measurement component 6 to perform measurement. More specifically, during the measurement time T2 from the voltage switch timing t2 until the voltage switch timing t3, the clock 11 is used to make 20 measurements at the measurement timings tm1, tm2, tm3, . . . , tmn, at a measurement interval of 100 ms, for example. Meanwhile, the count of the confirmation timer 12 is 3100 at the measurement timing tm1, 3200 at the measurement timing tm2, 3300 at the measurement timing tm3, and 5000 at the measurement timing tmn (the voltage switch timing t3 in this embodiment), according to the preset measurement timing.

The measurement operation performed during the measurement time T2 by the measurement device 100 pertaining to this embodiment will now be described.

The controller 7 first confirms that the measurement of the clock 11 is tm1 (S6 in FIG. 3).

At this point the controller 7 acquires the count of the confirmation timer 12 (S7 in FIG. 3).

It is then determined whether or not there is a discrepancy between the measurement timing preset for the measurement component 6 and the actual measurement timing (S8 in FIG. 3). More specifically, the controller 7 checks the count of the confirmation timer 12, and if the count is within, for example, 2% (±2 counts) with respect to the measurement timing in the measurement time T2 (a 100 ms interval), then the measured timing is deemed to be within the permissible range. That is, at the measurement timing tm1, when the count is within a range of 3098 to 3102, the timing of the measurement is within the permissible range, and the controller 7 determines that there is no discrepancy between the measurement timing preset for the measurement component 6 and the actual measurement timing.

If there is no discrepancy in the measurement timing, the voltage detected by the measurement component 6 is measured, and this measurement value is stored in the memory 10 (S9 in FIG. 3).

Thus, with the confirmation timer 12, the controller 7 can confirm whether or not the measurement executed using the clock 11 was executed properly at the measurement timing set by the controller 7 (that is, whether or not there is any discrepancy between the predetermined measurement timing and the actual measurement timing). As a result, there is less variance in the measurement result (which can occur in rare situations), and measurement accuracy can be improved.

Actual measurement is then repeated up until the measurement time T2 has elapsed, while continuing to determine whether or not there is a discrepancy in the measurement timing. This occurs from the measurement timing tm1 until the measurement timing tmn (S6 to S10 in FIG. 3 are executed repeatedly).

After this, the measurement component 6 calculates the blood glucose level on the basis of the plurality of acquired measurement values (S11 in FIG. 3).

The controller 7 stops the confirmation timer 12 and ends the blood glucose level measurement. This is the end of the measurement mode, and the measurement of the blood glucose level is completed (S12 in FIG. 3).

If the timing of the measurement is outside the permissible range in S8 in FIG. 3, this is a state in which there is a discrepancy between the preset measurement timing and the actual measurement timing. That is, although this very rarely happens as mentioned above, it is conceivable that a situation will occur in which measurement is not executed at the preset timing. The controller 7 in this embodiment connects to the display component 4 that displays information related to whether or not there is a discrepancy between the actual measurement timing and the preset measurement timing for the measurement component 6.

Therefore, if the measurement component 6 did not execute measurement on the basis of the measurement timing preset by the controller 7, the controller 7 instructs the display component 4 to give an error display (a display of information indicating that there is a discrepancy in the measurement timing) (S13 in FIG. 3).

This error display prompts the user to take another measurement, which allows the measurement to be executed properly. As a result, the very rare occurrence of variance in the measurement result can be suppressed even further, and measurement accuracy can be improved.

After this, the controller 7 returns to the process in S2 in FIG. 3, and the user mounts a fresh blood glucose level sensor 2 to the sensor mounting component 3 and takes another measurement. Even if there was a discrepancy in the measurement timing during the previous measurement, it is exceedingly unlikely that this will happen consecutively. Thus, the proper measurement will more than likely be carried out this time (S2 to S12 in FIG. 3).

In this embodiment, the confirmation timer 12 is actuated when the controller 7 goes into the measurement mode in S3 in FIG. 3 as discussed above. That is, it is actuated before actual measurement is performed to calculate the blood glucose level by the measurement component 6 (repetition of S6 to S10 in FIG. 3), and is halted when the measurement of the blood glucose level is completed (at the end of the measurement mode in S11 in FIG. 3). The confirmation timer 12 can be used in addition to being able to detect whether or not there is any discrepancy in the measurement timing that happens very rarely during measurement mode. When not in the measurement mode, the confirmation timer 12 can be used for other purposes which allows it to be utilized more effectively. Conversely, the timer that is used for such other purposes can be converted to use as a confirmation timer during the measurement mode.

Furthermore, in this embodiment, as discussed above, the clock 11 (first timer) is constituted of a quartz oscillator, and the confirmation timer (second timer) is constituted of a ceramic oscillator. That is, the two timers are made of different materials and use separate systems. Accordingly, the independence of each timer is higher, and it can be suitably confirmed with the confirmation timer 12 (another system) whether or not measurement using the clock 11 was properly executed at the measurement timing set by the controller 7. In this way, the measurement accuracy can be improved.

In this embodiment, as discussed above, the confirmation timer 12 connects to the controller 7, but the confirmation timer 12 may instead be provided integrally inside the controller 7. That is, since ceramic oscillators are smaller and less expensive than quartz oscillators, they are frequently used as a signal source or reference clock for the controller 7. When the controller 7 thus has a ceramic oscillator, if the confirmation timer 12 is provided integrally inside the controller 7, the ceramic oscillator inside the controller 7 can be utilized, and the confirmation timer 12 can have a simpler configuration.

Also, in this embodiment, the clock 11 being a quartz oscillator is used as the first timer, but a timer being a by a ceramic oscillator may instead be used as the first timer in measurement. As discussed above, a ceramic oscillator has sufficient precision within a few seconds of time (the measurement time), so the first timer can have a simpler configuration.

In this embodiment, an example was described in which measurement was based on a plurality of measurement timings, but this is not the only option. The configuration may be such that if measurement based on the preset measurement timing is performed even once in the measurement mode, it is determined whether or not there is a discrepancy in the measurement timing of the measurement component 6.

Also, the blood glucose level was used as an example of biological information, but that is not the only option. For instance, it may be a cholesterol value or the like, or some other information obtained from a biological sample, such as blood or saliva.

The measurement device 100 pertaining to this embodiment comprises the main case 1 including the sensor mounting component 3 (an example of a sensor mounting component) configured to mount the blood glucose level sensor 2 (an example of a sensor) that measures a blood glucose level (an example of biological information), the measurement component 6 (an example of a measurement component) that connects to the sensor mounting component 3, the controller 7 (an example of a controller) that connects to the measurement component 6, the clock 11 (an example of a first timer) that connects to the controller 7, and the confirmation timer 12 (an example of a second timer) that connects to the controller 7. The controller 7 has a measurement mode in which a measurement operation is performed through the measurement component 6, and in this measurement mode, the controller 7 executes the measurement operation based on a preset measurement timing using the clock 11, and determines the suitability of the measurement operation based on the preset measurement timing, using the confirmation timer 12.

With the measurement device 100 in this embodiment, the controller 7 executes a measurement operation based on the preset measurement timing using the clock 11 in the measurement mode, and the controller 7 connects to the confirmation timer 12 with which it can be confirmed as to whether or not the measurement operation has been executed properly at the measurement timing. Therefore, with the confirmation timer 12, it can be confirmed whether or not the measurement executed using the clock 11 is executed properly at the measurement timing set by the controller 7. As a result, the accuracy of blood glucose level measurement can be improved.

For example, when measurement by the measurement component 6 is not executed on the basis of the measurement timing set by the controller 7, the user is prompted to take another measurement, which allows the proper measurement to be executed. Thus, there is less variance in the measurement result (which can occur in rare situations).

An embodiment was described above as an example of the technology disclosed herein, and the appended drawings and detailed description were provided to that end.

Therefore, the constituent elements illustrated in the appended drawings and discussed in the detailed description can encompass not only those constituent elements that are essential to solving the problem, but also constituent elements that are not essential to solving the problem. Accordingly, just because these non-essential constituent elements are illustrated in the appended drawings and discussed in the detailed description, it should not be concluded that these non-essential constituent elements are essential.

Also, the above embodiments were given to illustrate examples of the technology disclosed herein, so various modifications, substitutions, additions, omissions, and so forth can be made within the scope of the patent claims or equivalents thereof.

INDUSTRIAL APPLICABILITY

This disclosure can be applied to any biological information measurement device for measuring biological information, such as the glucose level in blood.

The invention claimed is:

1. A biological information measurement device, comprising:
    a main case including a sensor mounting component configured to mount a sensor that senses biological information;
    a measurement component that connects to the sensor mounting component;
    a controller that connects to the measurement component;
    a first timer that connects to the controller; and
    a second timer that connects to the controller,
    wherein the controller has a measurement mode in which a measurement operation is performed through the measurement component, and
    in the measurement mode, the controller executes the measurement operation based on a preset measurement timing using the first timer, and uses the second timer to determine a suitability of the measurement operation based on the preset measurement timing.

2. The biological information measurement device according to claim 1,
    wherein in the measurement mode the controller determines whether or not there is a discrepancy between the preset measurement timing and an actual measurement timing of the measurement component.

3. The biological information measurement device according to claim 2, further comprising a display component that connects to the controller, wherein the controller causes the display component to display information indicating whether or not there is a discrepancy between the preset measurement timing and the actual measurement timing.

4. The biological information measurement device according to claim 1, wherein the second timer is actuated by the controller before the measurement operation is performed through the measurement component.

5. The biological information measurement device according to claim 1, wherein the second timer is constituted by a ceramic oscillator.

6. The biological information measurement device according to claim 5, wherein the second timer is provided integrally inside the controller.

7. The biological information measurement device according to claim 1, wherein the controller:
executes the measurement operation at a plurality of preset measurement timings in the measurement mode, and
uses the second timer to determine the suitability of each measurement operation based on the plurality of preset measurement timings.

8. The biological information measurement device according to claim 7, wherein in the measurement mode the controller determines whether or not there is a discrepancy between one or more preset measurement timings out of the plurality of preset measurement timings and a corresponding actual measurement timing when the measurement operation is executed on the basis of said one or more preset measurement timings.

9. A biological information measurement device, comprising:
a main case;
a sensor mounting component configured to mount a sensor that senses biological information;
a measurement component that connects to the sensor mounting component and measures the biological information;
a controller that connects to the measurement component and causes the measurement component to measure the biological information;
a first timer that connects to the controller and acquires at least one preset first measurement timing at which the measurement component measures the biological information; and
a second timer that connects to the controller and acquires a second measurement timing at which the measurement component measures the biological information on the basis of the first measurement timing,
wherein the controller:
determines a discrepancy between the preset first measurement timing and the second measurement timing, and
completes the measurement of the biological information by the measurement component only when the discrepancy is within a specific range.

10. The biological information measurement device according to claim 9, wherein the first timer and the second timer operate independently.

11. The biological information measurement device according to claim 9, wherein the controller executes a measurement mode for causing the measurement component to measure, and the second timer is actuated after the measurement mode is started.

12. The biological information measurement device according to claim 9, wherein the controller outputs error information when the discrepancy exceeds the specific range.

13. The biological information measurement device according to claim 9, wherein the preset first measurement timing and the second measurement timing each consist of a plurality of measurement timings, and
the controller determines the discrepancy between each preset first measurement timing and each corresponding second measurement timing, and completes the measurement of the biological information by the measurement component only when all of the discrepancies are within the specific range.

14. The biological information measurement device according to claim 9, wherein the controller outputs a result of the biological information measurement only when the discrepancy is within the specific range.

* * * * *